United States Patent
Baloa Welzien et al.

(10) Patent No.: US 8,960,192 B2
(45) Date of Patent: Feb. 24, 2015

(54) SYSTEM AND METHOD FOR QUANTIFYING LUNG COMPLIANCE IN A SELF-VENTILATING SUBJECT

(75) Inventors: Leonardo Alberto Baloa Welzien, Pittsburgh, PA (US); Nathan Francis O'Connor, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 358 days.

(21) Appl. No.: 13/386,434

(22) PCT Filed: Jul. 30, 2010

(86) PCT No.: PCT/IB2010/053490
§ 371 (c)(1),
(2), (4) Date: Jan. 23, 2012

(87) PCT Pub. No.: WO2011/027242
PCT Pub. Date: Mar. 10, 2011

(65) Prior Publication Data
US 2012/0145154 A1 Jun. 14, 2012

Related U.S. Application Data

(60) Provisional application No. 61/238,780, filed on Sep. 1, 2009.

(51) Int. Cl.
*A61B 5/08* (2006.01)
*A61M 16/00* (2006.01)
*A61M 16/16* (2006.01)

(52) U.S. Cl.
CPC .............. *A61B 5/08* (2013.01); *A61M 16/0051* (2013.01); *A61M 16/16* (2013.01);
(Continued)

(58) Field of Classification Search
CPC ..................... A61M 16/0051; A61M 2230/46; A61M 2016/027; A61M 2016/0033; A61M 2205/502; A61M 2205/15; A61M 2016/0021; A61M 16/0057; A61M 16/04; A61M 16/0666; A61M 16/0875; A61M 2230/42; A61M 16/16; A61M 2016/0024; A61M 2016/0036; A61M 2205/332; A61M 2205/3365; A61M 2205/505; A61M 2205/52; A61M 2230/43; A61B 5/08; A61B 5/085
USPC ............. 128/200.24, 204.18, 204.21, 204.23; 600/529, 532, 533, 538, 499
See application file for complete search history.

(56) References Cited

U.S. PATENT DOCUMENTS 4,031,885 A * 6/1977 Davis et al. ................... 600/533
6,105,575 A 8/2000 Estes et al.
(Continued)

FOREIGN PATENT DOCUMENTS

| JP | 2008000436 A | 1/2008 |
|----|---|---|
| WO | 2007134099 A2 | 11/2007 |
| WO | 2009039525 A2 | 3/2009 |
| WO | 2010070498 A1 | 6/2010 |

*Primary Examiner* — Annette Dixon

(57) ABSTRACT

The lung compliance of a subject that is at least partially self-ventilating is determined. The quantification of lung compliance may be an estimation, a measurement, and/or an approximate measurement. The quantification of lung compliance may be enhanced over conventional techniques and/ or systems for quantifying lung compliance of self-ventilating subjects in the lung compliance may be quantified relatively accurately without an effort belt or other external sensing device that directly measures diaphragmatic muscle pressure, and without requiring the subject to manually control diaphragmatic muscle pressure. Quantification of lung compliance may be a useful tool in evaluating the health of the subject, including detection of fluid retention associated with developing acute congestive heart failure.

15 Claims, 3 Drawing Sheets

(52) U.S. Cl.
CPC .............. *A61M 2016/0021* (2013.01); *A61M 2016/0024* (2013.01); *A61M 2016/0036* (2013.01); *A61M 2205/332* (2013.01); *A61M 2205/3365* (2013.01); *A61M 2205/505* (2013.01); *A61M 2230/42* (2013.01); *A61M 2230/43* (2013.01); *A61M 2230/46* (2013.01)
USPC ............ 128/204.23; 128/200.24; 128/204.18; 128/204.21

(56) References Cited

U.S. PATENT DOCUMENTS

| | | | |
|---|---|---|---|
| 7,530,353 B2 * | 5/2009 | Choncholas et al. | 128/204.18 |
| 8,418,691 B2 * | 4/2013 | Jafari et al. | 128/204.21 |
| 2008/0000478 A1 | 1/2008 | Matthiessen et al. | |

* cited by examiner

SYSTEM AND METHOD FOR QUANTIFYING LUNG COMPLIANCE IN A SELF-VENTILATING SUBJECT

BACKGROUND OF THE INVENTION

1. Field of the Invention

The invention relates to the quantification of lung compliance in a self-ventilating subject.

2. Description of the Related Art

Systems for quantifying (e.g., measuring, estimating, etc.) lung compliance in subjects are known. Such systems include ventilator systems configured to mechanically ventilate subjects completely. These systems may be implemented, for example, with subjects that are incapable of self-ventilation.

The quantification of lung compliance in a self-ventilating subject is dependent in part on diaphragmatic muscle pressure during respiration. As such, some systems configured to quantify lung compliance in subjects that are self-ventilating require the implementation of an effort belt, or some other sensor that provides a direct measurement of diaphragmatic muscle pressure. Other systems configured to quantify lung compliance in self-ventilating subjects require that the subject be directed and/or taught to control diaphragmatic muscle pressure manually. However, this typically requires the subject and/or doctor to perform a special maneuver which, if not performed with precision, may negatively impact the precision and/or accuracy of the estimation of lung compliance.

SUMMARY OF THE INVENTION

One aspect of the invention is related to a system configured to quantify lung compliance of a subject that is at least partially self-ventilating. In one embodiment, the system comprises a pressure support device, one or more sensors, and one or more processors. The pressure support device is configured to generate a pressurized flow of breathable gas to be delivered to the airway of a subject that is at least partially self-ventilating. The one or more sensors are configured to generate one or more output signals conveying information about one or more parameters of the pressurized flow of breathable gas. The one or more processors are operatively linked with the pressure support device and the one or more sensors, and are configured to execute one or more computer program modules. The one or more computer program modules comprise a control module, a pressure module, and a compliance module. The control module is configured to control the pressure support device to adjust pressure of the pressurized flow of breathable gas during a series of consecutive inhalations of the subject. The pressure module is configured to determine the pressure to which the pressurized flow of breathable gas should be adjusted by the control module during inhalations of the subject during the series of consecutive inhalations such that for a first inhalation the pressure is adjusted to a first pressure and for a second inhalation proximate in time to the first inhalation the pressure is adjusted to a second pressure that is different from the first pressure, wherein the pressure module randomly or pseudo randomly determines one or more of (i) the position of the first inhalation and the second inhalation within the series of inhalations, (ii) the first pressure, (iii) the second pressure, or (iv) a difference in pressure between the first pressure and the second pressure. The compliance module is configured to quantify lung compliance of the subject based on the difference between the first pressure and the second pressure and the one or more output signals generated by the one or more sensors during the first inhalation and the second inhalation.

Another aspect of the invention relates to a method of quantifying lung compliance of a subject that is at least partially self-ventilating. In one embodiment, the method comprises delivering a pressurized flow of breathable gas to the airway of a subject that is at least partially self-ventilating; generating one or more output signals conveying information about one or more parameters of the pressurized flow of breathable gas; determining pressures to which the pressurized flow of breathable gas should be adjusted during a series of consecutive inhalations of the subject, including determining a first pressure for a first inhalation and determining a second pressure for a second inhalation proximate in time to the first inhalation such that one or more of (i) the position of the first inhalation and the second inhalation within the series of inhalations, (ii) the first pressure, (iii) the second pressure, or (iv) a difference in pressure between the first pressure and the second pressure are determined randomly or pseudo randomly; adjusting the pressure of the pressurized flow of breathable gas to the determined pressures during the series of consecutive inhalations; and quantifying lung compliance of the subject based on the difference between the first pressure and the second pressure and the one or more output signals generated during the first inhalation and the second inhalation.

Another aspect of the invention relates to a system configured to quantify lung compliance of a subject that is at least partially self-ventilating. In one embodiment, the system comprises means for delivering a pressurized flow of breathable gas to the airway of a subject that is at least partially self-ventilating; means for generating one or more output signals conveying information about one or more parameters of the pressurized flow of breathable gas; means for determining pressures to which the pressurized flow of breathable gas should be adjusted during a series of consecutive inhalations of the subject, including means for determining a first pressure for a first inhalation and determining a second pressure for a second inhalation proximate in time to the first inhalation such that one or more of (i) the position of the first inhalation and the second inhalation within the series of inhalations, (ii) the first pressure, (iii) the second pressure, or (iv) a difference in pressure between the first pressure and the second pressure are determined randomly or pseudo randomly; means for adjusting the pressure of the pressurized flow of breathable gas to the determined pressures during the series of consecutive inhalations; and means for quantifying lung compliance of the subject based on the difference between the first pressure and the second pressure and the one or more output signals generated during the first inhalation and the second inhalation.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a

DETAILED DESCRIPTION OF EXEMPLARY EMBODIMENTS

Figure 1:
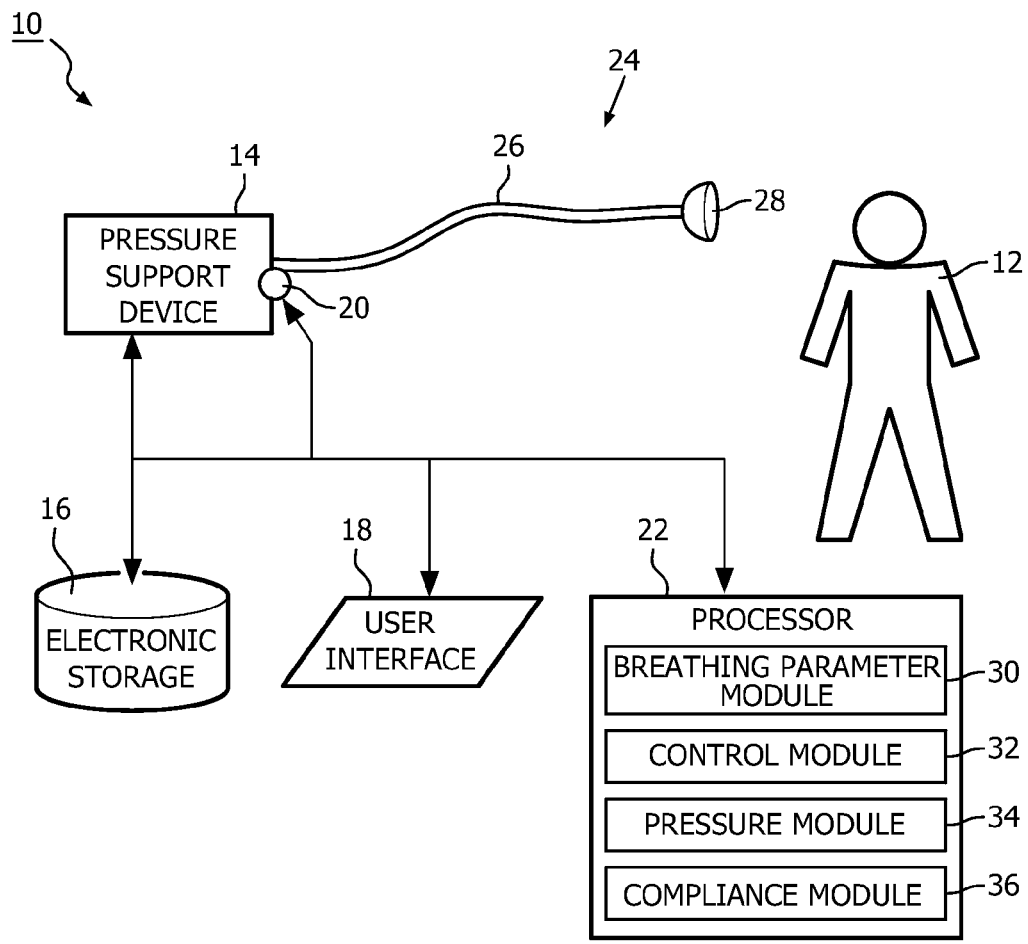
FIG. 1 illustrates a system configured to quantify lung compliance of a subject that is at least partially self-ventilating, according to one or more embodiments of the invention.

FIG. 1 illustrates a system 10 configured to quantify lung compliance of a subject 12 that is at least partially self-ventilating. The quantification of lung compliance may be an estimation, a measurement, and/or an approximate measurement. The quantification of lung compliance by system 10 may be enhanced over conventional systems for quantifying lung compliance of self-ventilating subjects in that system 10 may quantify lung compliance relatively accurately without an effort belt or other external sensing device that directly measures diaphragmatic muscle pressure. Quantification of lung compliance may be a useful tool in evaluating the health of subject 12, including detection of fluid retention associated with developing acute congestive heart failure. In one embodiment, system 10 includes one or more of a pressure support device 14, electronic storage 16, a user interface 18, one or more sensors 20, a processor 22, and/or other components.

In one embodiment, pressure support device 14 is configured to generate a pressurized flow of breathable gas for delivery to the airway of subject 12. The pressure support device 14 may control one or more parameters of the pressurized flow of breathable gas (e.g., flow rate, pressure, volume, humidity, temperature, composition, etc.) for therapeutic purposes, or for other purposes. By way of non-limiting example, pressure support device 14 may be configured to control the pressure of the pressurized flow of breathable gas to provide pressure support to the airway of subject 12. The pressure support device 14 may include a positive pressure support device such as, for example, the device described in U.S. Pat. No. 6,105,575, hereby incorporated by reference in its entirety.

The pressure support device 14 may be configured to generate the pressurized flow of breathable gas according to one or more modes. A non-limiting example of one such mode is Continuous Positive Airway Pressure (CPAP). CPAP has been used for many years and has proven to be helpful in promoting regular breathing. Another mode for generating the pressurized flow of breathable gas is Inspiratory Positive Air Pressure (IPAP). One example of the IPAP mode is bi-level positive air pressure mode (BIPAP®). In bi-level positive air pressure mode, two levels of positive air pressure (HI and LO) are supplied to a patient. Other modes of generating the pressurized flow of breathable gas are contemplated. Generally, the timing of the HI and LO levels of pressure are controlled such that the HI level of positive air pressure is delivered to subject 12 during inhalation and the LO level of pressure is delivered to subject 12 during exhalation.

The pressurized flow of breathable gas is delivered to the airway of subject 12 via a subject interface 24. Subject interface 24 is configured to communicate the pressurized flow of breathable gas generated by pressure support device 14 to the airway of subject 12. As such, subject interface 24 includes a conduit 26 and an interface appliance 28. Conduit conveys the pressurized flow of breathable gas to interface appliance 28, and interface appliance 28 delivers the pressurized flow of breathable gas to the airway of subject 12. Some examples of interface appliance 28 may include, for example, an endotracheal tube, a nasal cannula, a tracheotomy tube, a nasal mask, a nasal/oral mask, a full face mask, a total face mask, or other interface appliances that communication a flow of gas with an airway of a subject. The present invention is not limited to these examples, and contemplates delivery of the pressurized flow of breathable gas to subject 12 using any subject interface.

In one embodiment, electronic storage 16 comprises electronic storage media that electronically stores information. The electronically storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 22, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., device 14, user interface 18, processor 22, etc.).

User interface 18 is configured to provide an interface between system 10 and subject 12 through which subject 12 may provide information to and receive information from system 10. This enables data, results, and/or instructions and any other communicable items, collectively referred to as "information," to be communicated between the subject 12 and one or more of device 14, electronic storage 16, and/or processor 22. Examples of interface devices suitable for inclusion in user interface 18 include a keypad, buttons, switches, a keyboard, knobs, levers, a display screen, a touch screen, speakers, a microphone, an indicator light, an audible alarm, a printer, and/or other interface devices. In one embodiment, user interface 18 includes a plurality of separate interfaces. In one embodiment, user interface 18 includes at least one interface that is provided integrally with device 14.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

One or more sensors 20 are configured to generate one or more output signals conveying information related to one or more parameters of the pressurized flow of breathable gas. The one or more parameters may include, for example, one or more of a flow rate, a volume, a pressure, a composition (e.g., concentration(s) of one or more constituents), humidity, temperature, acceleration, velocity, acoustics, changes in a parameter indicative of respiration, and/or other gas parameters. The sensors 20 may include one or more sensors that measure such parameters directly (e.g., through fluid communication with the pressurized flow of breathable gas at pressure support device 14 or in subject interface 24). The sensors 20 may include one or more sensors that generate output signals related to one or more parameters of the pressurized flow of breathable gas indirectly. For example, one or more of sensors 20 may generate an output based on an operating parameter of pressure support device 14 (e.g., a motor current, voltage, rotational velocity, and/or other operating parameters), and/or other sensors. Although sensors 20 are illustrated at a single location at or adjacent to pressure support device 14, this is not intended to be limiting. The sensors 20 may include sensors disposed in a plurality of locations, such as for example, within pressure support device 14, within (or in communication with) conduit 26, within (or in communication with) interface appliance 28, and/or other locations.

Processor 22 is configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 22 may include a plurality of processing units. These processing units may be physically located within the same device (e.g., pressure support device 14), or processor 22 may represent processing functionality of a plurality of devices operating in coordination.

As is shown in FIG. 1, processor 22 may be configured to execute one or more computer program modules. The one or more computer program modules may include one or more of a breathing parameter module 30, a control module 32, a pressure module 34, a compliance module 36, and/or other modules. Processor 22 may be configured to execute modules 30, 32, 34, and/or 36 by software; hardware; firmware; some combination of software, hardware, and/or firmware; and/or other mechanisms for configuring processing capabilities on processor 22.

It should be appreciated that although modules 30, 32, 34, and 36 are illustrated in FIG. 1 as being co-located within a single processing unit, in implementations in which processor 22 includes multiple processing units, one or more of modules 30, 32, 34, and/or 36 may be located remotely from the other modules. The description of the functionality provided by the different modules 30, 32, 34, and/or 36 described below is for illustrative purposes, and is not intended to be limiting, as any of modules 30, 32, 34, and/or 36 may provide more or less functionality than is described. For example, one or more of modules 30, 32, 34, and/or 36 may be eliminated, and some or all of its functionality may be provided by other ones of modules 30, 32, 34, and/or 36. As another example, processor 22 may be configured to execute one or more additional modules that may perform some or all of the functionality attributed below to one of modules 30, 32, 34, and/or 36.

The breathing parameter module 30 is configured to determine one or more breathing parameters of the subject. The one or more breathing parameters are determined based on the one or more output signals generated by sensors 20. The one or more breathing parameters may include, for example, a tidal volume, a peak flow, a flow rate, a pressure, a composition, a timing (e.g., beginning and/or end of inhalation, beginning and/or end of exhalation, etc.), a duration (e.g., of inhalation, of exhalation, of a single breathing cycle, etc.), a breath rate, a respiration frequency, and/or other parameters. In one embodiment, breathing parameter module 30 determines the one or more breathing parameter on a per inhale and/or exhale basis. By way of non-limiting example, breathing parameter module 30 may determine at least one given breathing parameters for each exhalation in a series of consecutive exhalations. The at least one given breathing parameter may include, for instance, a tidal volume, a peak flow, and/or other breathing parameters.

The control module 32 is configured to control pressure support device 14 to adjust one or more parameters of the pressurized flow of breathable gas. For example, control module 32 may control pressure support device 14 to adjust a flow rate, pressure, volume, humidity, temperature, composition, and/or other parameters of the pressurized flow of breathable gas. In one embodiment, control module 32 controls pressure support device 14 to operate in a bi-level positive air pressure mode where pressure is elevated to a HI level during inhalation and reduced to a LO level during exhalation by subject 12. The control module 32 may determine when to trigger changes from HI to LO and vice versa based on detection of breathing transitions by breathing parameter module 30.

The pressure module 34 is configured to determine the pressure(s) to which the pressurized flow of breathable gas should be adjusted by control module 32. The pressure of the pressurized flow of breathable gas may be determined by pressure module 34 based on a therapy regime (e.g., for positive airway pressure support), to enable a quantification of lung compliance, and/or for other purposes. Determining the pressure(s) to which the pressurized flow of breathable gas should be adjusted includes determining the HI and LO pressure levels for a bi-level positive air pressure mode.

As is discussed further below, in order to enable a quantification of lung compliance, the pressure of pressurized flow of breathable gas should be changed between a pair of inhalations that are proximate to each other in time. As used herein, the pair of inhalations that are proximate in time to each other may include a pair of inhalations that are directly adjacent (i.e., consecutive without intervening inhalations), or a pair of inhalations that are reasonably close to each other in time (e.g., within about 2 minutes, within about 1 minute, within about 30 second, within about 15 seconds, etc.). To facilitate such a determination, pressure module 34 is configured to determine a first pressure to which the pressurized flow of breathable gas should be adjusted during a first inhalation, and a second pressure (different from the first pressure) to which the pressurized flow of breathable gas should be adjusted during a second inhalation that is proximate in time to the first inhalation. It will be appreciated that in some embodiments, the quantification of lung compliance may be based on measurements taken in two breaths that are not proximate in time. Although this may degrade the accuracy and/or precision of the quantification (due to assumptions made about patient physiology and/or respiratory conditions during the two breaths), such degradation may not be fatal to the usefulness of the quantification.

In embodiments in which system 10 is operating in a bi-level positive air pressure mode, control module 32 implements the first pressure as the HI pressure for the first inhalation, a LO pressure (determined by pressure module 34) for the exhalation(s) between the first inhalation and the second inhalation, and the second pressure as the HI pressure for the second inhalation. In embodiments in which system 10 is operating in a CPAP mode, control module 32 transitions between the first pressure and the second pressure at the breathing transition between the first inhalation and the exhalation after the first inhalation, at a point in time between the first inhalation and the second inhalation, or at the breathing transition between the exhalation before the second inhalation and the second inhalation.

As is discussed further below, in the quantification of lung compliance by system 10, the diaphragmatic muscle pressure of subject 12 is assumed to be the same for the first inhalation and the second inhalation. However, in some instances, if one or more of the transition timing, pressure level(s), and/or pressure difference, for the first pressure and the second pressure are done in a regular, periodic manner, subject 12 may begin to subconsciously anticipate this transition. In response to this anticipation, subject 12 may inadvertently adjust respiratory effort (and diaphragmatic muscle pressure) between the first inhalation and the second inhalation. To avoid this effect, pressure module 34 may determine the pressure to which the pressurized flow of breathable gas should be adjusted by control module 32 during a series of consecutive breaths including the first inhalation and the second inhalation such that one or more of (i) the position(s) of the first inhalation and/or the second inhalation in the series of consecutive breaths, (ii) the first pressure, (iii) the second pressure, and/or (iv) the difference between the first pressure and the second pressure may be determined in a random or pseudo random manner.

As used herein, the term "pseudo random" refers determinations of one or more of the parameters set forth above that approximate the properties of random number for the purposes of inhibiting anticipation by subject 12. This may include schemes in which a pseudo randomly determined parameter is determined with some periodicity and/or repeatability provided the period at which the parameter is repeated is large enough to avoid subconscious anticipation by subject 12.

Figure 2:
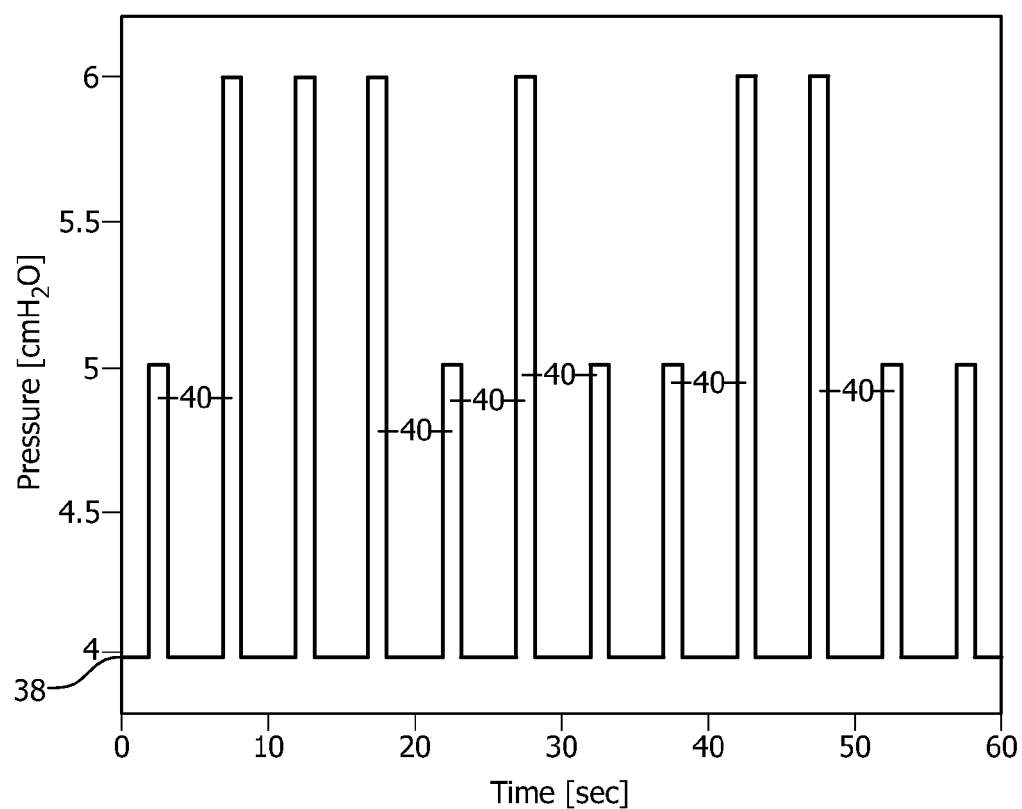
FIG. 2 illustrates a plot of pressure of a pressurized flow of breathable gas against time, in accordance with one or more embodiments of the invention.

By way of illustration, FIG. 2 illustrates a plot of pressure as determined by a pressure module similar to or the same as pressure module 34 vs. time over a series of consecutive breaths. During the series of consecutive breaths, pressure module 34 determines pressure of the pressurized flow of breathable gas in accordance with a bi-level positive air pressure mode in which pressure is reduced to a LO level 38 during exhalations. In the plot shown in FIG. 2, there a number of pairs of directly adjacent pairs of inhalations that could be viewed as the first and second inhalations described above. These pairs are labeled in FIG. 2 with reference numeral 40. The position and/or timing of these inhalation pairs having separate pressure values associated therewith is a random, or pseudo random, distribution designed to inhibit subject anticipation. Although not depicted in FIG. 2, from the foregoing it should be appreciated that in addition to determining the position and/or timing of the first and/or second inhalation within a series of consecutive breaths like the one shown in FIG. 2 in a random and/or pseudo random manner, one or more of the pressure(s) during the first inhalation and/or the second inhalation, and/or the pressure difference between the first inhalation and/or the second inhalation may be determined in a random and/or pseudo random manner.

Returning to FIG. 1, compliance module 36 is configured to quantify lung compliance of subject 12 based on the difference between the first pressure and the second pressure, and the one or more output signals generated by sensors 20 during the first and second inhalations. In one embodiment, compliance module 36 determines the lung compliance of subject 12 by removing diaphragmatic muscle pressure from input-output equations modeling the respiratory system of subject 12 during the first inhalation and the second inhalation.

Figure 3:
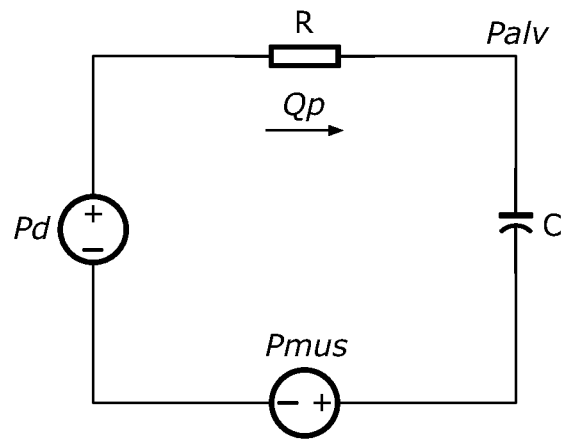
FIG. 3 is a schematic diagram of a lung-ventilator circuit, according to one or more embodiments of the invention.
Figure 4:
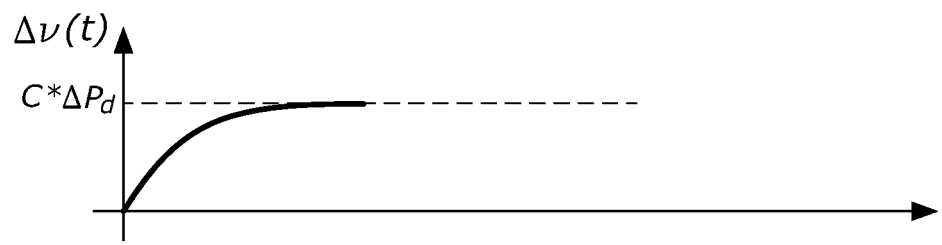
FIG. 4 illustrates a plot of volume difference against time during inhalation, in accordance with one or more embodiments of the invention.

In one embodiment, the quantification of lung compliance by compliance module 36 implements a single-compartment lung and ventilator circuit shown in FIG. 3. In FIG. 3 $P_d$ represents device pressure (e.g., the pressure of the pressurized flow of breathable gas generated by pressure support device 14), R represents the resistance of the respiratory system of a subject, $P_{alv}$ represents alveolar pressure, C represents compliance, $P_{mus}$ represents diaphragmatic muscle pressure, and $Q_p$ represents the subject flow. In FIG. 4, $\Delta v(t)$ represents the patient volume as function of time. C represents compliance of the subject and $\Delta P_d$ represents the measured change in device pressure from one breath to the next. In this model, it is assumed that the resistance of an exhalation port (e.g., exhalation port at interface appliance 28 in FIG. 1) is much greater than a resistance of a hose (e.g., conduit 26 in FIG. 1). Therefore, the pressure within the subject is approximately the same as the device pressure. Thus, subject pressure is simply represented as the device pressure in the circuit shown in FIG. 3. Further, it is assumed that the patient flow and patient volume can be estimated by using the difference between the measure total flow of the system and an estimated (or measured) leak flow.

It will be appreciated that the implementation of a single-compartment lung model in the description of determining lung compliance is not intended to be limiting. The removal of diaphragmatic muscle pressure from equations modeling the function of the respiratory system of a subject is not dependent on this model, but is used herein because it is computationally less expensive than more complex models, and simplifies explanation.

The transfer function in the s-domain relating patient flow to pressure of the device and the diaphragm of the subject for the circuit in FIG. 3 is given by:

$$\frac{Q_p(s)}{P(s)} = \frac{Cs}{RCs+1}, \quad (1)$$

where $$P(s) = P_d(s) + P_{mus}(s). \quad (2)$$

Additionally, the patient volume is given by the equation:

$$V(s) = \frac{Q_p(s)}{s}. \quad (3)$$

Thus, the transfer function relating the pressure to patient volume is given by the equation:

$$\frac{V(s)}{P(s)} = \frac{C}{RCs+1} \Rightarrow V(s) = \frac{C}{RCs+1} P_d(s) + \frac{C}{RCs+1} P_{mus}(s); \quad (4)$$

where the response to $P_{mus}$ is given by the equation:

$$V_{int}(s) = \frac{C}{RCs+1} P_{mus}(s); \quad (5)$$

and where the external response is given by:

$$V_{ext}(s) = \frac{C}{RCs+1} P_d(s). \quad (6)$$

Now, if $P_d(s)$ represents the pressure of the pressurized flow of breathable gas generated by a pressure support device, and the pressure during inhalation is varied between a first inhalation and a second inhalation that are proximate in time (e.g., directly adjacent), then equation (4) can be written for the first inhalation and the second inhalation in the following form:

$$V_1(s) = \frac{C}{RCs+1} P_{d1}(s) + \frac{C}{RCs+1} P_{mus1}(s); \text{ and} \quad (7)$$

$$V_2(s) = \frac{C}{RCs+1} P_{d2}(s) + \frac{C}{RCs+1} P_{mus2}(s); \quad (8)$$

where subscripts 1 and 2 correspond to the first inhalation and the second inhalation, respectively.

Since $P_{mus}$ is unknown, the part of the total response associated with the internal response is also unknown. However, if the assumption is made that $P_{mus}$ is relatively constant between the first inhalation and the second inhalation (since the first and second inhalations are proximate in time), then $P_{mus1}(s)$ can be assumed to be equal to $P_{mus2}(s)$.

Taking the difference between the volume responses in equations (5) and (6), and using the assumption that $P_{mus1}(s)$ is equal to $P_{mus2}(s)$, the unknown internal response can be eliminated to yield the following combination of equations (7) and (8):

$$\Delta V(s) = \frac{C}{RCs+1} \Delta P_d(s); \quad (9)$$

where $\Delta V(s)$ is the difference between $V_1(s)$ and $V_2(s)$, and where $\Delta P_d(s)$ is the difference between $P_{d1}(s)$ and $P_{d2}(s)$.

Since the pressures and volumes, for the two inhalations (and/or the instantaneous differences therebetween) are known, any one of various known numerical estimation techniques can be used to determine resistance R and compliance C. By way of non-limiting example, the technique of least squared error could be implemented.

Returning to FIG. 1, compliance module 36 may quantify lung compliance based on breathing parameter(s) determined by breathing parameter module 30 (which are determined from output signals generated by sensors 20), the known value(s) of the first pressure, the second pressure, and/or the difference between the first pressure and the second pressure in the manner described above. This quantification may then be implemented for one or more of a variety of different uses and/or in a variety of different contexts. For example, the quantification of lung compliance may be implemented to preemptively diagnose congestive heart failure, to prescribe treatment, and/or for other purposes.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to quantify lung compliance of a subject that is at least partially self-ventilating, the system comprising:
   a pressure support device configured to generate a pressurized flow of breathable gas to be delivered to the airway of the subject that is at least partially self-ventilating;
   one or more sensors configured to generate one or more output signals conveying information about one or more parameters of the pressurized flow of breathable gas; and
   one or more processors operatively linked with the pressure support device and the one or more sensors, the one or more processors being configured to execute one or more computer program modules, the one or more computer program modules comprising:
   a control module configured to control the pressure support device to adjust pressure of the pressurized flow of breathable gas during a series of consecutive inhalations of the subject;
   a pressure module configured to determine the pressure to which the pressurized flow of breathable gas should be adjusted by the control module during inhalations of the subject during the series of consecutive inhalations such that for a first inhalation the pressure is adjusted to a first pressure and for a second inhalation proximate in time to the first inhalation the pressure is adjusted to a second pressure that is different from the first pressure, wherein the pressure module randomly or pseudo randomly determines one or more of (i) the position of the first inhalation and the second inhalation within the series of inhalations, (ii) the first pressure, (iii) the second pressure, or (iv) a difference in pressure between the first pressure and the second pressure;
   a compliance module configured to quantify lung compliance of the subject based on the difference between the first pressure and the second pressure and the one or more output signals generated by the one or more sensors during the first inhalation and the second inhalation.

2. The system of claim 1, wherein the first pressure and the second pressure are fixed, and wherein the pressure module is configured to determine the pressure to which the pressurized flow of breathable gas should be adjusted by the control module during inhalations of the subject during the series of consecutive inhalations such that for each inhalation in the series of consecutive inhalations the pressure is determined by the pressure module to be either the first pressure or the second pressure.

3. The system of claim 1, wherein the pressure module is further configured to determine the pressure to which the pressurized flow of breathable gas should be adjusted by the control module during exhalations of the subject between the series of consecutive inhalations is lower than the first pressure and is lower than the second pressure.

4. The system of claim 1, wherein the one or modules further comprise a breathing parameter module configured to determine, based on the one or more output signals of the one or more sensors, one or more breathing parameter of the subject during the series of consecutive inhalations, and wherein the compliance module is configured to quantify lung compliance of the subject based on the difference between the first pressure and the second pressure and the one or more breathing parameters determined by the breathing parameter module during the first inhalation and the second inhalation.

5. The system of claim 4, wherein the one or more breathing parameters determined by the breathing parameter module that are implemented by the compliance module to quantify lung compliance of the subject comprise tidal volume.

6. A method of quantifying lung compliance of a subject that is at least partially self-ventilating, the method comprising:
    delivering a pressurized flow of breathable gas to the airway of the subject that is at least partially self-ventilating;
    generating one or more output signals conveying information about one or more parameters of the pressurized flow of breathable gas;
    determining pressures to which the pressurized flow of breathable gas should be adjusted during a series of consecutive inhalations of the subject, including determining a first pressure for a first inhalation and determining a second pressure for a second inhalation proximate in time to the first inhalation such that one or more of (i) the position of the first inhalation and the second inhalation within the series of inhalations, (ii) the first pressure, (iii) the second pressure, or (iv) a difference in pressure between the first pressure and the second pressure are determined randomly or pseudo randomly;
    adjusting the pressure of the pressurized flow of breathable gas to the randomly or pseudo randomly determined pressures during the series of consecutive inhalations; and
    quantifying lung compliance of the subject based on the difference between the first pressure and the second pressure and the one or more output signals generated during the first inhalation and the second inhalation.

7. The method of claim 6, wherein the first pressure and the second pressure are fixed, and wherein determining pressures to which the pressurized flow of breathable gas should be adjusted during a series of consecutive inhalations of the subject includes selecting between the first pressure and the second pressure for each inhalation in the series of consecutive inhalations.

8. The method of claim 6, further comprising adjusting the pressure of the pressurized flow of breathable gas during exhalations of the subject between the series of consecutive inhalations to a pressure that is lower than the first pressure and is lower than the second pressure.

9. The method of claim 6, further comprising determining, based on the one or more output signals, one or more breathing parameter of the subject during the series of consecutive inhalations, and wherein quantifying lung compliance of the subject based on the difference between the first pressure and the second pressure and the one or more output signals generated during the first inhalation and the second inhalation comprises quantifying lung compliance of the subject based on the difference between the first pressure and the second pressure and the one or more breathing parameters determined during the first inhalation and the second inhalation.

10. The method of claim 9, wherein the one or more breathing parameters comprise tidal volume.

11. A system configured to quantify lung compliance of a subject that is at least partially self-ventilating, the system comprising:
    means for delivering a pressurized flow of breathable gas to the airway of the subject that is at least partially self-ventilating;
    means for generating one or more output signals conveying information about one or more parameters of the pressurized flow of breathable gas;
    means for determining pressures to which the pressurized flow of breathable gas should be adjusted during a series of consecutive inhalations of the subject, including means for determining a first pressure for a first inhalation and determining a second pressure for a second inhalation proximate in time to the first inhalation such that one or more of (i) the position of the first inhalation and the second inhalation within the series of inhalations, (ii) the first pressure, (iii) the second pressure, or (iv) a difference in pressure between the first pressure and the second pressure are determined randomly or pseudo randomly;
    means for adjusting the pressure of the pressurized flow of breathable gas to the randomly or pseudo randomly determined pressures during the series of consecutive inhalations; and
    means for quantifying lung compliance of the subject based on the difference between the first pressure and the second pressure and the one or more output signals generated during the first inhalation and the second inhalation.

12. The system of claim 11, wherein the first pressure and the second pressure are fixed, and wherein the means for determining pressures to which the pressurized flow of breathable gas should be adjusted during a series of consecutive inhalations of the subject includes means for selecting between the first pressure and the second pressure for each inhalation in the series of consecutive inhalations.

13. The system of claim 11, further comprising means for adjusting the pressure of the pressurized flow of breathable gas during exhalations of the subject between the series of consecutive inhalations to a pressure that is lower than the first pressure and is lower than the second pressure.

14. The system of claim 11, further comprising means for determining, based on the one or more output signals, one or more breathing parameter of the subject during the series of consecutive inhalations, and wherein the means for quantifying lung compliance of the subject based on the difference between the first pressure and the second pressure and the one or more output signals generated during the first inhalation and the second inhalation quantifies lung compliance of the subject based on the difference between the first pressure and the second pressure and the one or more breathing parameters determined during the first inhalation and the second inhalation.

15. The system of claim 14, wherein the one or more breathing parameters comprise tidal volume.

* * * * *